(12) United States Patent
Lee et al.

(10) Patent No.: US 9,429,506 B2
(45) Date of Patent: Aug. 30, 2016

(54) APPARATUS AND METHOD OF MEASURING EFFECTIVE POROSITY USING RADON

(71) Applicant: KOREA INSTITUTE OF GEOSCIENCE AND MINERAL RESOURCES, Daejeon (KR)

(72) Inventors: Kilyong Lee, Daejeon (KR); Kyoochul Ha, Daejeon (KR)

(73) Assignee: KOREA INSTITUTE OF GEOSCIENCE AND MINERAL RESOURCES, Daejeon (KR)

( * ) Notice: Subject to any disclaimer, the term of this patent is extended or adjusted under 35 U.S.C. 154(b) by 363 days.

(21) Appl. No.: 14/095,651

(22) Filed: Dec. 3, 2013

(65) Prior Publication Data

US 2015/0068285 A1    Mar. 12, 2015

(30) Foreign Application Priority Data

Sep. 6, 2013   (KR) .................. 10-2013-0107469

(51) Int. Cl.
*G01N 15/08*    (2006.01)
*G01N 33/00*    (2006.01)

(52) U.S. Cl.
CPC ......... *G01N 15/088* (2013.01); *G01N 33/0011* (2013.01)

(58) Field of Classification Search
CPC .............. G01N 33/0011; G01N 15/088
USPC ....................................................... 73/23.2
See application file for complete search history.

(56) References Cited

U.S. PATENT DOCUMENTS

| 2005/0061737 A1* | 3/2005 | Linden .............. A01K 63/04 210/602 |
| 2015/0068276 A1* | 3/2015 | Lee .................. G01N 33/0006 73/23.2 |

FOREIGN PATENT DOCUMENTS

| JP | 2004-157068 | 6/2004 |
| JP | 2008-203268 | 9/2008 |

(Continued)

OTHER PUBLICATIONS

Office Action issued by the Japanese Patent Office on Jan. 6, 2015.

(Continued)

*Primary Examiner* — John Fitzgerald
*Assistant Examiner* — David Z Huang
(74) *Attorney, Agent, or Firm* — IP & T Group LLP

(57) ABSTRACT

The present invention relates to an apparatus and method of measuring effective porosity of various media such as rock or soil using radon that is an inert gas. An apparatus of measuring porosity according to the present invention includes: a gas component detector having two ports and configured to measure a concentration of a predetermined gas; a gas vessel having two ports and configured to accommodate the predetermined gas; a medium vessel having two ports and configured to accommodate a medium, of which the porosity is desirous to be measured; pipe lines connecting the ports of the gas component detector, the gas vessel and the medium vessel; and valves installed on the pipe lines.

17 Claims, 7 Drawing Sheets

(56) References Cited

FOREIGN PATENT DOCUMENTS

| | | |
|---|---|---|
| JP | 2011-209079 | 10/2011 |
| JP | 2013-032956 | 2/2013 |
| KR | 100477010 | 3/2005 |
| KR | 101057142 | 8/2011 |

OTHER PUBLICATIONS

Lee, K. Y., et al., Determination of air-loop volume and radon partition coefficient for measuring radon in water sample, Journal of Radioanalytical and Nuclear Chemistry, May 21, 2013.

Notice of Allowance issued by the Korean Intellectual Property Office on Dec. 23, 2014.

\* cited by examiner

APPARATUS AND METHOD OF MEASURING EFFECTIVE POROSITY USING RADON

CROSS-REFERENCE TO RELATED APPLICATIONS

The present application claims priority from Korean Patent Application No. 10-2013-0107469 filed on Sep. 6, 2013, which is incorporated herein by reference in its entirety.

BACKGROUND OF THE INVENTION

1. Field of Invention

The present invention relates to an apparatus and method of measuring effective porosity using radon, and more particularly, to an apparatus and method of measuring effective porosity of various media such as rock or soil using radon that is an inert gas.

2. Description of the Prior Art

The porosity of rock, which refers to a capability of storing fluid, provides a basis for determining economic feasibility of petroleum, natural gas, subsurface water, or mineral resource and is used in a variety of fields other than that, and thus, it is very important to accurately calculate the porosity.

For example, recently, studies on underground storage of carbon dioxide for solving global warming are actively carried out, and an investigation for selecting proposed sites for storing carbon dioxide is performed along therewith. In order to find an underground storage place of carbon dioxide in a commercialized scale, evaluations for a scale of a quantitative storage space and a storage capacity should be carried out. To this end, it is preferentially required to find a stratum having a porosity of at least 8%.

In addition, weathering and permeability of rock plays an important role in terms of stability securement and long-term management of a bedrock structure and disposal of radioactive waste in subterranean caves. The weathering and permeability of rock is greatly influenced depending on internal structure properties of the rock. That is, the weathering may proceed rapidly depending on the quantity of pores, fine cracks and the like inside rock. In addition, a quantitative evaluation of an internal structure of rock may be a means capable of quantitatively evaluating the degree of weathering of the rock. Therefore, in terms of long-term management of a bedrock structure, it is very important to accurately understand the internal structure of rock in three dimensions.

Carbonate rock is very important reservoir rock, and the understanding of lithological properties of carbonate rock is very important in evaluating economic feasibility of a mining area and oil deposits. Particularly, techniques of analyzing and predicting permeability of carbonate reservoir rock may be helpfully used in greatly reducing capital risk when developing a mining area. The permeability of carbonate reservoir rock is mainly influenced by porosity of reservoir rock, connectivity between pores, temperature of reservoir rock, precipitation of asphaltene and the like. However, it has been known that among the factors, the porosity of reservoir rock most greatly influences the permeability of reservoir rock.

The liquid substances in the ground permeate through pores connected between soil particles constituting the ground. In addition, it has been known that the liquid substances in bedrock moves depending on cracks and fine cracks formed by weathering, fault activity, discontinuity surface, joint, and the like. Therefore, all spaces connected to one another that relate to a mechanism of such movement may be represented as spatial meaning of the effective porosity. The effective porosity is one of the very important parameters capable of estimating a contaminant penetration pathway, the subsurface water content, and the like.

Even in order to evaluate the subsurface water content in the ground for rain and the inflow of contaminants leaked from the ground surface, it is preferentially necessary to understand porosity and effective porosity, which are physical properties of the ground. Further, in the case of subsurface dam in the course of construction in an alluvium region that is an unconsolidated, unconfined aquifer for the purpose of emerging conservation and effective use of water resources, in order to estimate storage capability of subsurface water in the target area, the measurement of porosity and effective porosity of the ground should be preceded.

The porosity may be classified into absolute porosity or total porosity and effective porosity depending on whether or not geotechnically isolated pores are included. The absolute porosity is a ratio of the volume of all empty spaces in a sample to the total volume thereof with or without connectivity between the spaces. On the contrary, the effective porosity is defined as a ratio of the total volume of the pores connected to one another allowing fluid to pass, except isolated pores, to the total volume.

Indoor measurement of porosity of rock is generally performed using a saturation method. According to the definition of porosity, it can be seen that the porosity calculated by a saturation method is effective porosity. The volume of pores is calculated using a difference in weight between a saturated state and a dried state of rock according to the saturation method. Thus, the accuracy in measuring the porosity depends on whether rock is saturated 100%. In Korean Society for Rock Mechanics and International Society for Rock Mechanics, a saturation method using vacuum is employed as a standard test method, in which a test specimen is immersed in water in a vacuum state below 800 Pa (6 torr) for one or more hours to saturate the test specimen.

Here, when a vacuum pump with low pumping rate is used or a plurality of test specimens are saturated in a lump, the test specimens should be immersed in water for a long time in a vacuum state. Particularly, if a test specimen contains substances soluble in water, a surface-dried water saturation weight is reduced. In addition, there may be various disadvantages according to the vacuumization by the water-immersion. One of the disadvantages is air bubbles captured on the surface of the test specimen when it is immersed in water and saturated. In the standard test, the test specimen is periodically disturbed in order to remove the air bubbles, which is practically extremely difficult operation. Moreover, vacuum efficiency is deteriorated and influenced even by the amount of water because of water serving as buffer along with the air.

SUMMARY OF THE INVENTION

Accordingly, the present invention is conceived to solve the aforementioned problems in the prior art. An objective of the present invention is to provide an apparatus and method of relatively simply and accurately measuring porosity of various media using radon.

According to an aspect of the present invention for achieving the objectives, there is provided an apparatus of measuring porosity, including: a gas component detector having two ports and configured to measure a concentration of a predetermined gas; a gas vessel having two ports and configured to accommodate the predetermined gas; a medium vessel having two ports and configured to accommodate a medium, of which the porosity is desirous to be measured; pipe lines connecting the ports of the gas component detector, the gas vessel and the medium vessel; and valves installed on the pipe lines, wherein the pipe lines and the valves are arranged and installed to form a first loop wherein the gas component detector is not connected to both the gas vessel and the medium vessel, a second loop wherein the gas component detector is connected to the gas vessel and not connected to the medium vessel, and a third loop wherein the gas component detector is connected to the medium vessel and not connected to the gas vessel, and the valves switches between the loops.

Preferably, the two ports of the gas component detector are respectively connected to the two ports of the gas vessel through two pipe lines, the valves are respectively installed on the two pipe lines, the valves are connected to each other through a pipe line, the valves are respectively connected to the two ports of the medium vessel through two pipe lines, and each of the valves is a four-way valve.

Preferably, the gas component detector, the gas vessel, and the medium vessel are serially connected to one another through pipe lines to form a single closed loop, the valves are respectively installed at the pipe lines in the vicinity of the two ports of the gas vessel and connected to each other through a pipe line, the valves are respectively installed at the pipe lines in the vicinity of the two ports of the medium vessel and connected to each other through a pipe line, and each of the valves is a three-way valve.

The apparatus may further include a pump installed adjacent to the gas component detector.

The gas component detector and the pump may be integrally formed.

Each port of the gas vessel may be provided with an opening/closing valve.

The apparatus may further include a drying tube installed on the first loop.

The apparatus may further include a drying tube installed on the third loop.

The predetermined gas may include at least one of radon and helium.

According to another aspect of the present invention, there is provided a method of measuring porosity, including: providing the above-described apparatus of measuring porosity, accommodating the predetermined gas and the medium, of which the porosity is desirous to be measured, in the gas vessel and the medium vessel, respectively; forming the second loop and maintaining it for a predetermined time; forming the first loop, maintaining it for a predetermined time, and measuring a concentration of the predetermined gas in the first loop by the gas component detector; forming the third loop, maintaining it for a predetermined time so that pores of the medium are filled with the predetermined gas, and measuring a concentration of the predetermined gas in the third loop by the gas component detector; and calculating porosity of the medium based on the respective gas concentrations in the first and third loops, respective internal volumes of these loops, a volume of the medium, and a mass balance equation for the predetermined gas in these loops.

Before the second loop is formed, the method may further include additionally forming the first loop to measure a background concentration of the predetermined gas in the additional first loop by the gas component detector, wherein after forming the second loop, the gas concentrations measured in the first and third loops by the gas component detector are corrected by subtracting the background concentration therefrom.

The predetermined gas may include at least one of radon and helium.

A solid substance generating the predetermined gas may be accommodated in the gas vessel.

A drying tube may be further installed on the first loop of the apparatus of measuring porosity, and before forming the second loop, the method may further include additionally forming the first loop to allow air to circulate in the first loop, thereby removing moisture within the third loop.

A drying tube may be further installed on the third loop of the apparatus of measuring porosity, and before forming the second loop, the method may further include additionally forming the third loop to allow air to circulate in the third loop, thereby removing moisture within the third loop.

BRIEF DESCRIPTION OF THE DRAWINGS

The above and other objectives, features and advantages of the present invention will become apparent from the following description of a preferred embodiment given in conjunction with the accompanying drawings, in which.

DETAILED DESCRIPTION OF THE PREFERRED EMBODIMENT

Figure 1:
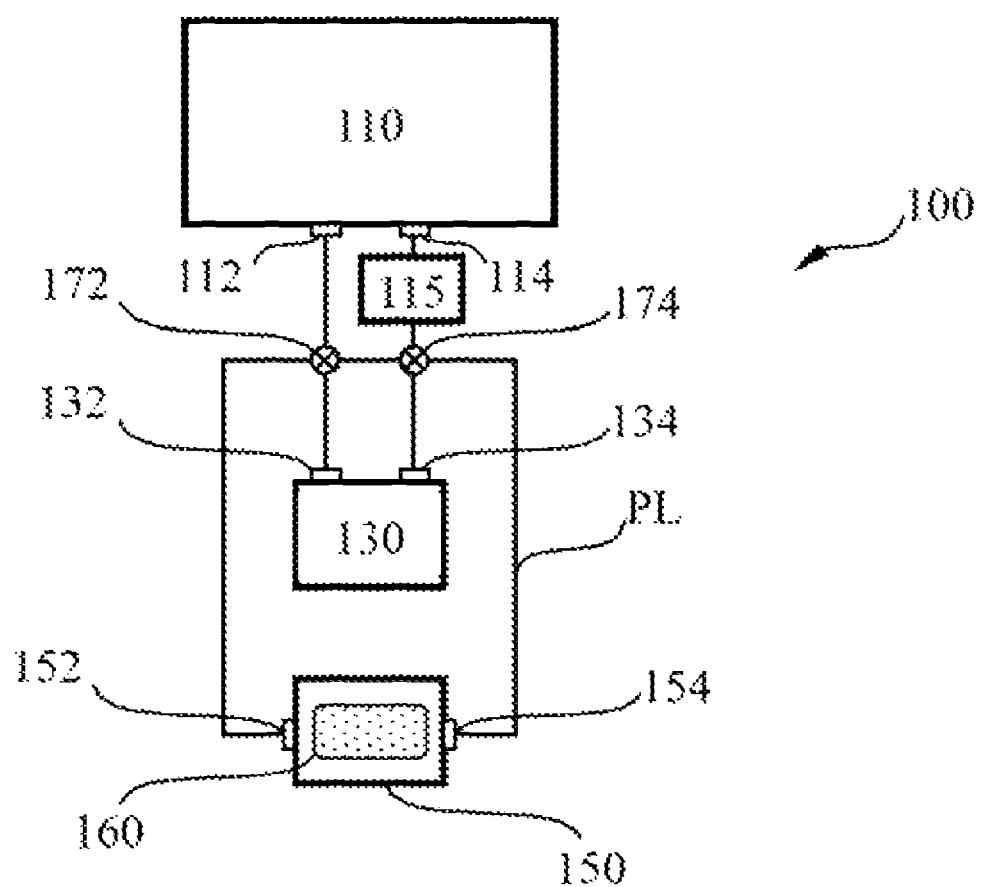
FIG. 1 is a schematic view of an apparatus of measuring porosity of a medium according to an embodiment of the present invention.

Hereinafter, preferred embodiments of the present invention will be described in detail with reference to the accompanying drawings. The following embodiments are provided only for illustrative purposes so that those skilled in the art can fully understand the spirit of the present invention. Therefore, the present invention is not limited to the following embodiments but may be implemented in other forms. In the drawings, the widths, lengths, thicknesses and the like of elements may be exaggerated for convenience of illustration. Like reference numerals indicate like elements throughout the specification and drawings.

Figure 2:
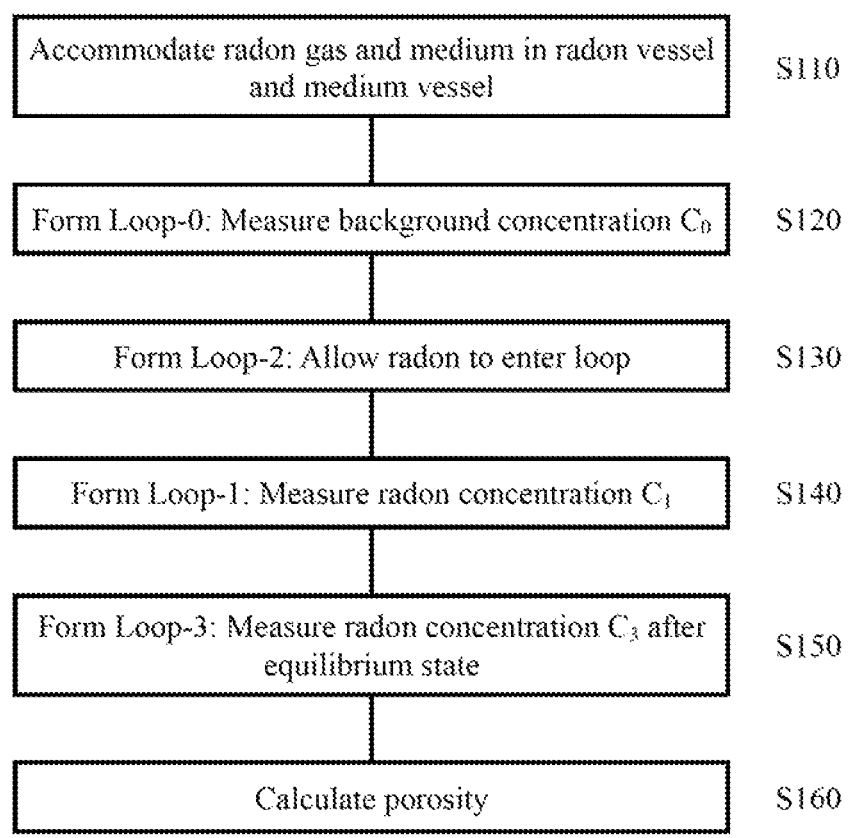
FIG. 2 is a flowchart illustrating a method of measuring porosity of a medium using the apparatus shown in FIG. 1.

FIG. 1 is a schematic view of an apparatus of measuring porosity of a medium according to an embodiment of the present invention; FIG. 2 is a flowchart illustrating a method of measuring porosity of a medium using the apparatus shown in FIG. 1; and FIGS. 3A to 3D are views showing loops formed in respective steps for measuring porosity of a medium using the apparatus shown in FIG. 1.

First, referring to FIG. 1, a porosity measuring apparatus 100 according to an embodiment of the present invention includes a radon component detector 110 for measuring the concentration of radon gas, a drying tube 115, a radon vessel 130 for accommodating radon gas, a medium vessel 150 for accommodating a medium 160, of which the porosity is desirous to be measured, pipe lines PL for connecting the radon component detector 110, the radon vessel 130 and the medium vessel 150 to one another, and a plurality of valves 172 and 174 installed at predetermined positions of the pipe lines PL to switch between a plurality of predetermined loops formed by the radon component detector 110, the radon vessel 130, the medium vessel 150, and the pipe lines PL. Unless otherwise specified herein, radon refers to radon (Rn-220).

The radon component detector 110 is a pump built-in type and includes a component detection part for detecting the concentration of radon gas and input and out ports 112 and 114 respectively connected to pipe lines PL. Since the radon component detector 110 used in the embodiment has a pump installed therein, the pump operates to allow radon gas to flow into the radon component detector 110 through the pipe line PL connected to the input port 112 and to allow the radon gas to flow out through the output port 114 after the concentration of the radon gas is measured by the component detection part.

The drying tube 115 is optionally provided in order to remove moisture from the radon component detector 110, the medium vessel 150, and/or the medium 160. The drying tube 115 is filled with a desiccant, which changes color if the desiccant contains moisture. It is possible to confirm a dried state from a ratio of a discolored desiccant with moisture contained therein to a desiccant without moisture. Although in the embodiment, the drying tube 115 is disposed adjacent to the radon component detector 110, the present invention is not limited thereto, but the drying tube 115 may be disposed at any other various positions. However, in order to remove moisture from the radon component detector 110, it is preferred that the drying tube 115 be disposed adjacent to the radon component detector 110.

The radon vessel 130, which is an airtight container for accommodating radon gas, accommodates radon gas itself, but it may be preferred that a solid substance generating radon gas, such as a radon-enriched mineral, be accommodated in the radon vessel 130. The radon vessel 130 is provided with two ports 132 and 134, which in turn are respectively connected to the pipe lines PL. The two ports 132 and 134 of the radon vessel 130 are preferably equipped with opening/closing valves.

The medium vessel 150 is an airtight container for accommodating the medium 160, of which the porosity is desirous to be measured. The medium vessel 150 is provided with two ports 152 and 154, which in turn are respectively connected to the pipe lines PL.

The input and output ports 112 and 114 of the radon component detector 110 are respectively connected to the two ports 132 and 134 of the radon vessel 130 through the two pipe lines PL. Here, the valves 172 and 174 are respectively installed in the middles of the two pipe lines PL, and the valves 172 and 174 are connected to each other through a pipe line PL. In addition, the valves 172 and 174 are connected to the two ports 152 and 154 of the medium vessel 150 through the pipe lines PL. Here, each of the valves 172 and 174 installed in the pipe lines PL is a four-way valve.

By controlling the valves 172 and 174 in the state that the pipe lines PL and the valves 172 and 174 are connected and installed, predetermined loops Loop-0, Loop-1, Loop-2 and Loop-3 for measuring the radon concentration necessary for calculating the porosity of the medium 160.

Figure 3A:
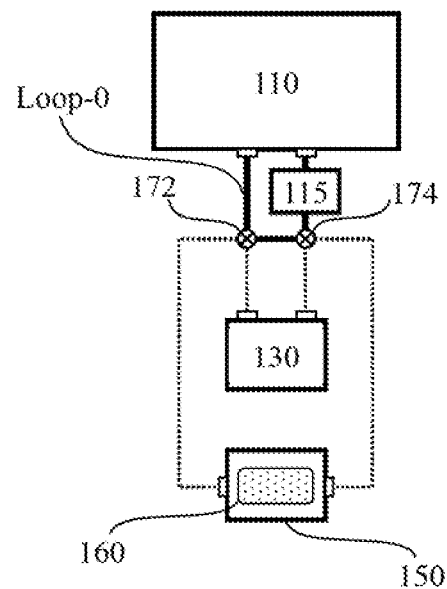
FIGS. 3A to 3D are views showing loops formed in respective steps for measuring porosity of a medium using the apparatus shown in FIG. 1.
Figure 3B:
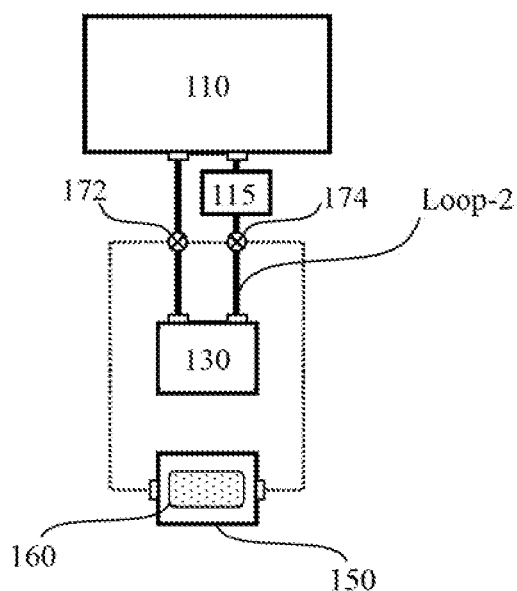
Figure 3C:
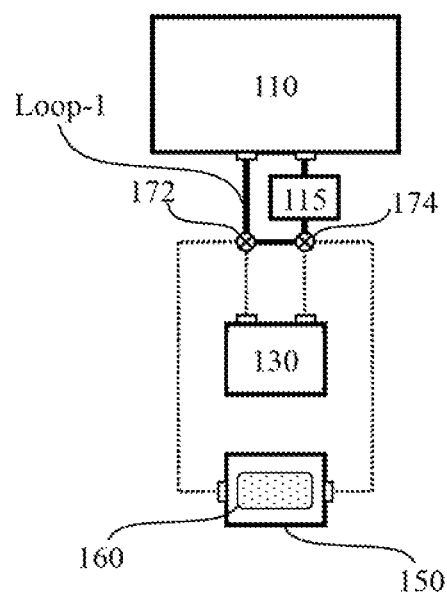
Figure 3D:
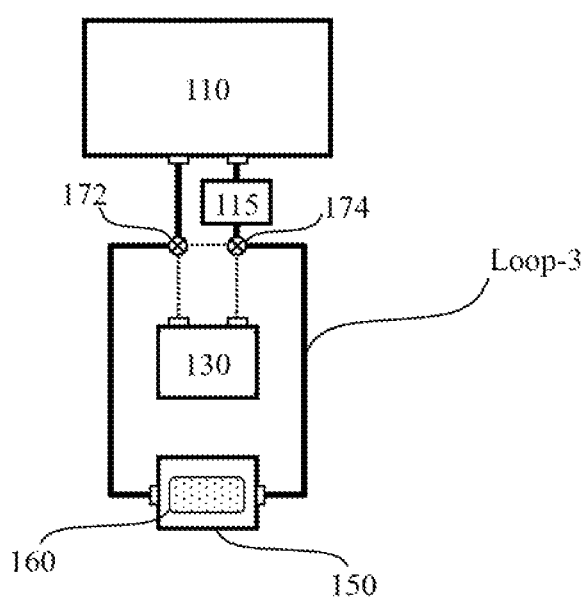

That is, by controlling the valves 172 and 174, the loop Loop-0 or Loop-1 (i.e., a closed loop connecting reference numerals 110, 172, 174, 115 and 110 in the embodiment) is formed so that the radon component detector 110 is not connected to both the radon vessel 130 and the medium vessel 150 as shown by a bold line in FIG. 3A or 3C, the loop Loop-2 (i.e., a closed loop connecting reference numerals 110, 172, 130, 174, 115 and 110 in the embodiment) is formed so that the radon component detector 110 is connected to the radon vessel 130 and not connected to the medium vessel 150 as shown by a bold line in FIG. 3B, and the loop Loop-3 (i.e., a closed loop connecting reference numerals 110, 172, 150, 174, 115 and 110 in the embodiment) is formed so that the radon component detector 110 is connected to the medium vessel 150 and not connected to the radon vessel 130 as shown by a bold line in FIG. 3D.

Here, the internal volumes of the loops Loop-1 and Loop-3 among the loops are used in calculating the porosity of the media. It should be noted that the internal volumes of the loops Loop-1 and Loop-3 include the volume of the internal path of the radon component detector 110 from the input port 112 to the output port 114 thereof, the volume (except the volume of the desiccant) of the internal space of the drying tube 115, the volume of the internal space of the medium vessel 150, the volume of the medium 160, and/or the volume of the internal spaces of the valves 172 and 174 in addition to the internal volume of the corresponding pipe lines PL. As the internal volume of each loop, only a macroscopic space in the loop is basically taken into consideration. Therefore, in the case of the loop Loop-3 including the medium vessel 150, the volume of the internal space of the medium vessel 150 is a volume obtained by subtracting the entire volume of the medium 160 disposed in the medium vessel 150 from the entire internal volume of the medium vessel 150.

Next, a method of measuring the porosity of the medium 160 using the measuring apparatus 100 so configured will be described with reference to FIGS. 2 and 3A to 3D.

First, radon gas or radon-enriched mineral and a medium 160 are accommodated in the radon vessel 130 and the medium vessel 150, respectively (S110). Here, the measuring apparatus 100 should be in the state of the loop Loop-0, in which the input port 112 of the radon component detector 110 is connected to the output port 114 thereof via the drying tube 115 through the pipe lines PL as shown in FIG. 3A by operating the valves 172 and 174 in order for the radon component detector 110 not to be connected to the radon vessel 130 and the medium vessel 150. Here, if an opening/closing valve is installed at each of the ports 132 and 134 of the radon vessel 130 and is in a closed state, the measuring apparatus 100 may be in a state of any loop. Here, the accommodated medium 160 should be in a sufficiently dried state in order for moisture not to occur within the pores of the medium 160.

Then, the radon component detector 110 is operated in the state of the loop Loop-0 as shown in FIG. 3A. Here, the air of a measuring room occurs in the loop Loop-0 so configured. While the air circulates in the loop Loop-0 by means of the pump provided in the radon component detector 110 in the operation thereof, the component detection part of the radon component detector 110 measures the background concentration $C_0$ of radon gas that essentially occurs in the air in the loop Loop-0 (S120). That is, the background concentration $C_0$ of radon gas refers to the concentration of the radon gas that essentially occurs in the measuring room, specifically in the measuring apparatus 100 and the pipe lines PL. The concentration of radon gas in the loop Loop-1 or Loop-3 formed later can be more precisely obtained by subtracting the background concentration $C_0$ from the radon concentration measured in each loop. However, if the background concentration of radon gas can be obtained from the information about the measuring room, the step of measuring the background concentration $C_0$ may be omitted.

Here, since the loop Loop-0 includes the drying tube 115, while the air circulating in the loop Loop-0 passes through the drying tube 115, the moisture in the radon component detector 110 and the pipe lines PL is removed. It is preferred that the background concentration $C_0$ of radon gas be measured after allowing the air to circulate in the loop Loop-0 until the relative humidity in the loop Loop-0 including the radon component detector 110 is less than 5%.

Meantime, the order of the step S110 of respectively accommodating the radon gas and the medium in the radon vessel 130 and the medium vessel 150 and the step S120 of measuring the background concentration $C_0$ of radon gas may be changed.

Thereafter, the loop Loop-2, in which the radon component detector 110 and the radon vessel 130 are connected to each other as shown in FIG. 3B, is formed by operating the valves 172 and 174, thereby allowing the radon gas concentrated in the radon vessel 130 to enter the loop Loop-2 (S130). Here, if the ports 132 and 134 of the radon vessel 130 are respectively provided with opening/closing valves, these valves should be in an open state. By maintaining the loop Loop-2 for about 10 minutes, the radon gas is allowed to uniformly occur in the loop Loop-2. Here, it is possible to allow the radon gas to circulate in the loop Loop-2 and rapidly reach the uniform state by operating the pump of the radon component detector 110.

Then, the loop Loop-1, in which the input port 112 of the radon component detector 110 is connected to the output port 114 thereof via the drying tube 115 through the pipe lines PL as shown in FIG. 3C, is formed by operating the valves 172 and 174. After maintaining the loop Loop-1 for a predetermined time, the component detection part of the radon component detector 110 measures the radon concentration $C_1$ in the loop Loop-1 (S140). Here, it is preferred that the radon concentration $C_1$ measured in the loop Loop-1 be corrected by subtracting the background concentration $C_0$ of radon gas measured in the step S120 therefrom. In practice, since the loops Loop-0 and Loop-1 have the same route but contain the substances having different concentrations, the loops Loop-0 and Loop-1 are expressed differentially from each other.

Thereafter, the loop Loop-3, in which the radon component detector 110, the drying tube 115 and the medium vessel 150 are connected to one another as shown in FIG. 3D, is formed by operating the valves 172 and 174. Then, after the radon gas reaches an equilibrium state in the loop Loop-3, the radon concentration $C_3$ in the loop Loop-3 is measured (S150). Here, the equilibrium state means that if the loop Loop-3 is formed as shown in FIG. 3D, the radon gas that has existed in the loop Loop-1 is introduced into the medium vessel 150 through the loop Loop-3, and the pores of the medium 160 accommodated in the medium vessel 150 is filled with a portion of the introduced radon gas. That is, the measured radon concentration $C_3$ is a value measured after the pores of the medium 160 is completely filled with radon gas. Here, it is also preferred that the radon concentration $C_3$ measured in the loop Loop-3 be corrected by subtracting the background concentration $C_0$ of radon gas measured in the step S120 therefrom.

If the radon concentrations $C_1$, and $C_3$ in the loops Loop-1 and Loop-3 are measured as described above, the porosity is calculated according to the following procedure (S160).

A mass balance equation for radon gas in the loops Loop-1 and Loop-3 is as follows:

$$C_1 * V_1 = C_3 * (V_3 + V_p) \quad \text{(Equation 1)}$$

wherein $C_1$ and $C_3$ are respectively the radon concentrations in the loops Loop-1 and Loop-3, $V_1$ and $V_3$ are respectively the internal volumes of the loops Loop-1 and Loop-3, and $V_p$ is the volume of the pores of the medium 160 accommodated in the medium vessel 150. As described above, $C_1$ and $C_3$ are respectively measured in steps S140 and S150, and $V_1$ and $V_3$ may be obtained from the volume of the internal path of the radon component detector 110, the volume of the internal space (except the volume of the desiccant) of the drying tube 115, the volume of the internal space (except the volume of medium) of the medium vessel 150, and the internal volume of the pipe lines PL, which will be described later again.

If Equation 1 is rearranged to solve for $V_p$, which is the volume of the pores in the medium, the following Equation 2 is obtained as follows:

$$V_p = V_1 * C_1 / C_3 - V_3 \quad \text{(Equation 2)}$$

Therefore, according to the definition of porosity, the porosity P is calculated as follows:

$$\begin{aligned} P(\%) &= 100 * V_p / V_m \quad \text{(Equation 3)} \\ &= 100 * ((C_1 * V_1)/(C_3 * V_m) - V_3/V_m) \end{aligned}$$

wherein, $V_m$ is the volume of the medium 160.

In the meantime, $V_1$ and $V_3$ may be calculated as follows.

First, the internal volume $V_1$ of the loop Loop-1, which connects reference numerals 110, 172, 174, 115 and 110, is the sum of the volume of the internal path of the radon component detector 110 from the input port 112 to the output port 114 thereof, the volume of the internal space (except the volume of the desiccant) of the drying tube 115, the internal volume of the pipe lines PL from the input port 112 of the radon component detector 110 to the output port 114 of the radon component detector 110 via the valves 172 and 174 and the drying tube 115, and the volume of the internal path of the valves 172 and 174. The volume of the internal path of each of the radon component detector 110 and the valves 172 and 174 and the volume of the internal space (except the volume of the desiccant) of the drying tube 115 may be obtained from its specification or a conventional method such as a weight method, and the internal volume of the pipe line PL may be obtained using its inner diameter and length or from a weight method.

The weight method is used to obtain the internal volume of the pipe line PL by filling the pipe line PL with a fluid, the density of which is known, such as distilled water, and then obtaining the internal volume of the pipe line PL from the mass of the distilled water.

The internal volume $V_3$ of the loop Loop-3, which connects reference numerals 110, 172, 150, 174, 115 and 110, is the sum of the volume of the internal path of the radon component detector 110 from the input port 112 to the output port 114 thereof, the volume (except the volume of the desiccant) of the internal space of the drying tube 115, the internal volume of the pipe lines PL from the input port 112 of the radon component detector 110 to the output port 114 of the radon component detector 110 via the valve 172, the medium vessel 150, the valve 174 and the drying tube 115, the volume obtained by subtracting the volume $V_m$ of the medium 160 from the internal volume of the medium vessel 150, and the volume of the internal path of the valves 172 and 174. The volume of the internal path of the radon component detector 110, the internal volume of the pipe lines PL and the volume of the internal path of the valves 172 and 174 each may be obtained in the same manner as described above, and the internal volume of the medium vessel 150 may be obtained from the specification thereof or a conventional method such as a weight method.

The internal volume of each component may be obtained using various methods other than the aforementioned methods. For example, the internal path volume of the radon component detector 110 may be obtained using the apparatus of the present invention as follows.

Using the aforementioned apparatus 100, some (S120 to S150) of the steps of the aforementioned porosity measuring method is preformed in a state where the medium vessel 150 is filled with no media, i.e., in a state of the empty vessel. That is, radon gas is accommodated in the radon vessel 130, the background concentration $C_0$ of radon gas is measured in the loop Loop-0 shown in FIG. 3A (corresponding to S120), the loop Loop-2 is formed as shown in FIG. 3B and the radon gas is uniformly distributed in the loop Loop-2 (corresponding to S130); the loop Loop-1 is formed as shown in FIG. 3C and the concentration $C_1$ of the radon gas is measured therein (corresponding to S140); and the loop Loop-3 is formed as shown in FIG. 3D and maintained for a predetermined time and the concentration $C_3$ of the radon gas is measured in the loop Loop-3 (corresponding to S150). Thereafter, the internal path volume of the radon component detector 110 may be calculated according to the following procedure.

A mass balance equation for the radon gas in the loops Loop-1 and Loop-3 is as follows:

$$C_1 * V_1 = C_3 * V_3 \quad \text{(Equation 4)}$$

The internal volumes $V_1$ and $V_3$ of the loops Loop-1 and Loop-3 each may be specifically subdivided as follows.

The internal volume $V_1$ of the loop Loop-1 is the sum of the internal path volume $V_d$ of the radon component detector 110, the internal volume $V_{P1}$ of the pipe lines PL constituting the loop Loop-1, and the volume $V_V$ of the internal path of both the valves 172 and 174. That is, $V_1 = V_d + V_{P1} + V_V$.

The internal volume $V_3$ of the loop Loop-3 is the sum of the internal path volume $V_d$ of the radon component detector 110, the internal volume $V_{P3}$ of the pipe lines PL constituting the loop Loop-3, the internal volume $V_E$ of the empty vessel 150, and the volume $V_V$ of the internal path of both the valves 172 and 174. That is, $V_3 = V_d + V_{P3} + V_E + V_V$.

The following Equation 5 is obtained by substituting $V_1$ and $V_3$ into Equation 4.

$$C_1 * (V_d + V_{P1} + V_V) = C_3 * (V_d + V_{P3} + V_E + V_V) \quad \text{(Equation 5)}$$

If Equation 5 is rearranged to solve for the internal path volume $V_d$ of the radon component detector 110, the internal path volume $V_d$ is obtained as follows:

$$V_d = (C_3 * (V_{P3} + V_E) - C_1 * V_{P1} + (C_3 - C_1) * V_V) / (C_1 - C_3) \quad \text{(Equation 6)}$$

Meanwhile, in the above-described embodiment, although the radon component detector 110 and the valves 172 and 174 may be individually operated by an operator, an additional controller may be provided to automatically perform the above-described measurement steps after the radon gas and the medium 160 are respectively accommodated in the radon vessel 130 and the medium vessel 150.

Figure 4:
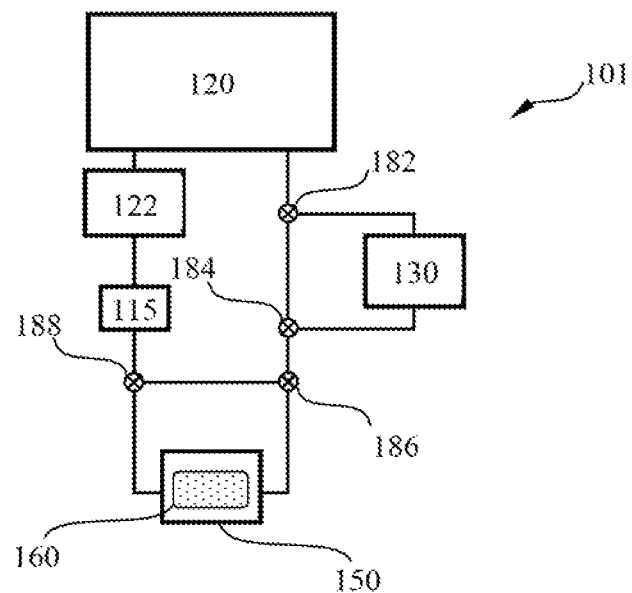
FIG. 4 is a schematic view of an apparatus of measuring porosity of a medium according to a modified embodiment of the present invention.

Next, an apparatus of measuring porosity of a medium according to a modified embodiment of the present invention will be described. FIG. 4 is a schematic view of an apparatus of measuring porosity of a medium according to a modified embodiment of the present invention; and FIGS. 5A to 5D are views showing loops formed in respective steps for measuring porosity of a medium using the apparatus shown in FIG. 4.

Referring to FIG. 4, a porosity measuring apparatus 101 according to the modified embodiment of the present invention includes a radon component detector 120 for measuring the concentration of radon gas, a pump 122, a drying tube 115, a radon vessel 130 for accommodating radon gas, a medium vessel 150 for accommodating a medium 160, of which the porosity is desirous to be measured, pipe lines PL for connecting the above-described components, and a plurality of valves 182, 184, 186 and 188 installed at predetermined positions of the pipe lines PL to switch between a plurality of predetermined loops formed by the radon component detector 120, the pump 122, the drying tube 115, the radon vessel 130, the medium vessel 150, and the pipe lines PL.

The radon component detector 120 is the same as the radon component detector 110 of the previous embodiment except that the radon component detector 120 does not have a pump housed therein. The radon component detector 120 corresponds to the component detection part of the radon component detector 110 of the previous embodiment, and the pump 122 corresponds to the pump of the radon component detector 110. That is, the radon component detector 120 and the pump 122 of the modified embodiment, into which the component detection part and the pump housed in the radon component detector 110 of the previous embodiment are separated, are substantially the same as the radon component detector 110. In the apparatus of measuring porosity of a medium according to the present invention, since the pump serves to assist radon gas in the formed loop in being uniform in the loop, the pump is a substantially optional element. Therefore, the pump 122 may be omitted in the modified embodiment, and the radon component detector 110 may also have no pump housed therein in the previous embodiment.

The drying tube 115, the radon vessel 130 and the medium vessel 150 are respectively the same as the drying tube 115, the radon vessel 130 and the medium vessel 150 of the previous embodiment.

The radon component detector 120, the pump 122, the drying tube 115, the radon vessel 130 and the medium vessel 150 are connected to one another through the pipe lines PL so that they serially form one closed loop. In addition, there are further provided paths, which do not pass through the radon vessel 130 and the medium vessel 150 but bypath them, respectively. That is, the valves 182 and 184 are respectively installed at the pipe lines PL in the vicinity of the two ports of the radon vessel 130 and connected to each other through a pipe line PL, and the valves 186 and 188 are respectively installed at the pipe lines PL in the vicinity of the two ports of the medium vessel 150 and connected to each other through a pipe line PL.

By controlling the valves 182, 184, 186 and 188 in the state that the pipe lines PL and the valves 182, 184, 186 and 188 are connected to one another and installed as described above, loops Loop-0, Loop-1, Loop-2 and Loop-3 each having the same path as those of the previous embodiment may be formed.

Figure 5A:
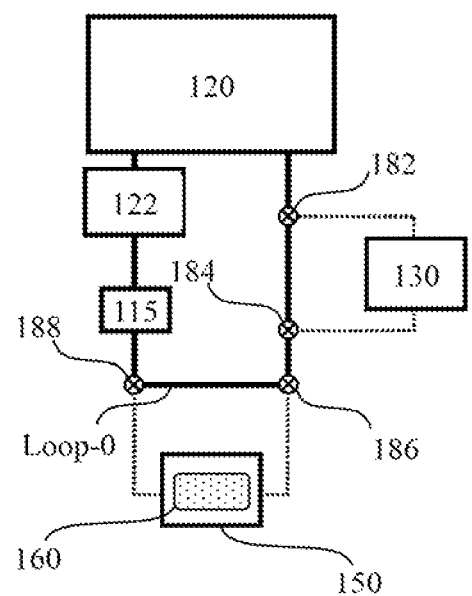
FIGS. 5A to 5D are views showing loops formed in respective steps for measuring porosity of a medium using the apparatus shown in FIG. 4.
Figure 5B:
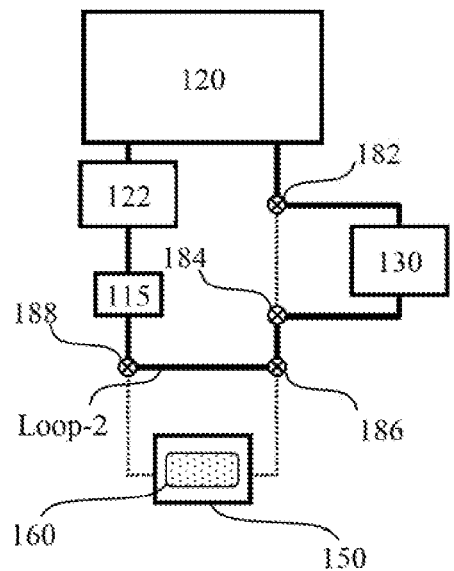
Figure 5C:
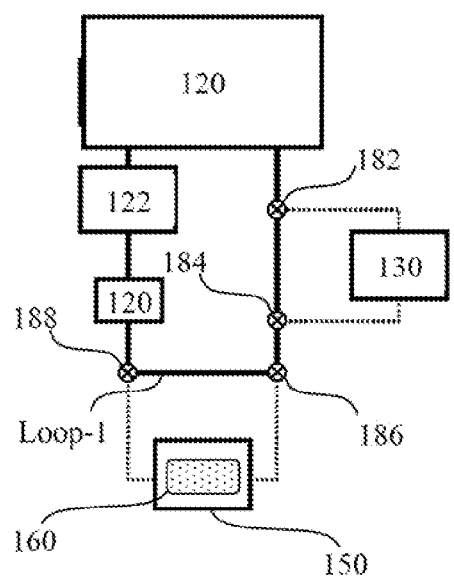
Figure 5D:
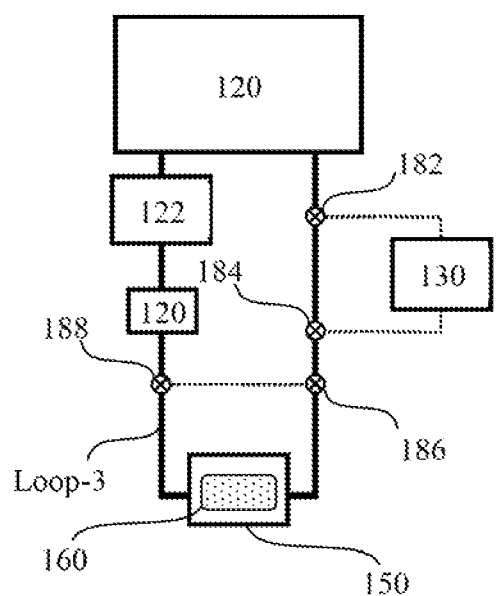

That is, by controlling the valves 182, 184, 186 and 188, the loop Loop-0 or Loop-1 (i.e., a closed loop connecting reference numerals 120, 182, 184, 186, 188, 115, 122 and 120 in the modified embodiment) is formed so that the radon component detector 120 is not connected to both the radon vessel 130 and the medium vessel 150 as shown by a bold line in FIG. 5A or 5C, the loop Loop-2 (i.e., a closed loop connecting reference numerals 120, 182, 130, 184, 186, 188, 115, 122 and 120 in the modified embodiment) is formed so that the radon component detector 120 is connected to the radon vessel 130 and not connected to the medium vessel 150 as shown by a bold line in FIG. 5B, and the loop Loop-3 (i.e., a closed loop connecting reference numerals 120, 182, 184, 186, 150, 188, 115, 122 and 120 in the modified embodiment) is formed so that the radon component detector 120 is connected to the medium vessel 150 and not connected to the radon vessel 130 as shown by a bold line in FIG. 5D.

In the modified embodiment, the connection configuration of the pipe lines and the valves is somewhat changed and the number of the valves is increased, as compare with the previous embodiment. The valves used in the modified embodiment are increased in number and are not four-way valves but three-way valves.

Substantially, if the valves 182 and 188 are combined and substituted by one four-way valve and the valves 184 and 186 are combined and substituted by one four-way valve, the modified embodiment has the same configuration as the previous embodiment.

A method of measuring porosity of a medium using the measuring apparatus 101 so configured is the same as the measuring method described in the previous embodiment.

That is, radon gas and a medium are respectively accommodated in the radon vessel 130 and the medium vessel 150 (S110); the radon component detector 110 is dried and then the background concentration $C_0$ of radon gas is measured in the loop Loop-0 shown in FIG. 5A (S120); the loop Loop-2 is formed as shown in FIG. 5B and the radon gas is uniformly distributed in the loop Loop-2 (S130); the loop Loop-1 is formed as shown in FIG. 5C and the radon concentration $C_1$ is measured therein (S140) and the loop Loop-3 is formed as shown in FIG. 5D and the concentration $C_3$ of the radon gas that reaches an equilibrium state in the loop Loop-3 is measured (S150). If the radon concentrations $C_1$ and $C_3$ are measured as described above, the porosity P is calculated using the above-described Equation 3 (S160).

In this modified embodiment, although the radon component detector 120, the pump 122, and the valves 182, 184, 186 and 188 may be individually operated by an operator, an additional controller may be provided to automatically perform the above-described measurement steps after the radon gas and the medium 160 are respectively accommodated in the radon vessel 130 and the medium vessel 150.

Meanwhile, if the respective components, i.e., the radon component detector 110 or 120, the drying tube 115, the radon vessel 130, the medium vessel 150, the pipe lines PL and the valves are connected to one another to form the loops Loop-0, Loop-1, Loop-2 and Loop-3, they may be changed in positions, order and/or number to be modified into any other forms. However, when the pump 122 is included, it is preferred that the pump 122 be installed adjacent to the radon component detector 120.

In the meantime, since the drying tube 115 is installed adjacent to the radon component detector 110 or 120, in the state that the loop Loop-0 is formed, the air is allowed to circulate in the loop Loop-0 to remove the moisture inside the radon component detector 110 or 120, thereby making it possible to more accurately measure the concentration. After the loop Loop-0 is formed, the loop Loop-3 is formed before the loop Loop-2 is formed, and an additional step of allowing the air to circulate in the loop Loop-3 may be further performed. In such a case, even though the medium 160 was not sufficiently dried in the step S110 of accommodating the medium 160 in the medium vessel 150, the more accurate porosity of the medium 160 can be obtained by removing the moisture contained in the medium vessel 150 and the medium 160 accommodated therein by means of the drying tube 115 in the above-described additional step. Here, since the loop Loop-3 of the additional step is before the loop Loop-2 is formed, the loop Loop-3 contains the air in the measuring room. That is, the loop Loop-3 of the additional step has the same route as the loop Loop-3 formed in the step S150 but contains compositions different therefrom.

According to the present invention, the concentration of radon gas changes as the pores of the medium are filled with the radon gas, and, based on such a change, the porosity of the medium is measured. Radon is generated from three types of naturally occurring radioactive decay series, i.e., uranium series (U-238), actinium series (U-235) and thorium series (Th-232), and radon occurs in the form of three isotopes, i.e., Rn-222 (having a half-life of 3.82 days), Rn-219 (having a half-life of 3.96 seconds) and Rn-220 (having a half-life of 55.6 seconds). Among the three radon isotopes, Rn-222 having the longest half-life of 3.82 days is commonly referred to as radon, and the radon used in the present invention is Rn-222.

The reason that in the present invention, radon is selected as the gas with which pores of a medium are filled is because the concentration of radon (Rn-222) can be relatively simply and accurately obtained by measuring radioactivity of radon. Instead of radon, helium (He) may be used as the gas with which pores of a medium are filled.

In addition, it can be seen that from the definition of porosity that the porosity calculated in such a manner is effective porosity.

An apparatus and method of measuring porosity of a medium using radon according to the present invention so configured is simple in constitution, and thus, it is possible to simply and accurately measure porosity of various media.

Particularly, since the porosity can be measured not in a vacuum state but an atmospheric pressure state, the measuring procedure is simple and the measuring time is also very short. Further, since radon (Rn-222) that is an inert gas is used and thus does not have a chemical reaction with the medium, it is possible to accurately measure the porosity.

Also, since radon generated from the uranium series that is one of the naturally occurring radioactive series and is a radioactive nuclide having a half-life of 3.82 days, it is possible to relatively simply and accurately measure porosity of a medium by measuring radioactivity of radon and using it.

Although some embodiments of the present invention are described for illustrative purposes, it will be apparent to those skilled in the art that various modifications and changes can be made thereto within the scope of the invention without departing from the essential features of the invention. Accordingly, the aforementioned embodiments should be construed not to limit the technical spirit of the present invention but to be provided for illustrative purposes so that those skilled in the art can fully understand the spirit of the present invention. The scope of the present invention should not be limited to the aforementioned embodiments but defined by appended claims. The technical spirit within the scope substantially identical with the scope of the present invention will be considered to fall in the scope of the present invention defined by the appended claims.

What is claimed is:

1. An apparatus flail for measuring porosity, comprising:
   a gas component detector having two ports and configured to measure a concentration of a predetermined gas;
   a gas vessel having two ports and configured to accommodate the predetermined gas;
   a medium vessel having two ports and configured to accommodate a medium, of which the porosity is desirous to be measured;
   pipe lines connecting the ports of the gas component detector, the gas vessel and the medium vessel; and
   valves installed on the pipe lines,
   wherein the pipe lines and the valves are arranged and installed to form a first loop wherein the gas component detector is not connected to both the gas vessel and the medium vessel, a second loop wherein the gas component detector is connected to the gas vessel and not connected to the medium vessel, and a third loop wherein the gas component detector is connected to the medium vessel and not connected to the gas vessel, and the valves switches between the loops.

2. The apparatus according to claim 1, wherein the two ports of the gas component detector are respectively connected to the two ports of the gas vessel through two pipe lines, the valves are respectively installed on the two pipe lines, the valves are connected to each other through a pipe line, the valves are respectively connected to the two ports of the medium vessel through two pipe lines, and each of the valves is a four-way valve.

3. The apparatus according to claim 2, further comprising a pump installed adjacent to the gas component detector.

4. The apparatus according to claim 1, wherein the gas component detector, the gas vessel, and the medium vessel are serially connected to one another through pipe lines to form a single closed loop, the valves are respectively installed at the pipe lines in the vicinity of the two ports of the gas vessel and connected to each other through a pipe line, the valves are respectively installed at the pipe lines in the vicinity of the two ports of the medium vessel and connected to each other through a pipe line, and each of the valves is a three-way valve.

5. The apparatus according to claim 4, further comprising a pump installed adjacent to the gas component detector.

6. The apparatus according to claim 1, further comprising a pump installed adjacent to the gas component detector.

7. The apparatus according to claim 6, wherein the gas component detector and the pump are integrally formed.

8. The apparatus according to claim 1, wherein each port of the gas vessel is provided with an opening/closing valve.

9. The apparatus according to claim 1, further comprising a drying tube installed on the first loop.

10. The apparatus according to claim 1, further comprising a drying tube installed on the third loop.

11. The apparatus according to claim 1, wherein the predetermined gas comprises at least one of radon and helium.

12. A method of measuring porosity, comprising:
    ng the apparatus for measuring porosity according to claim 1;
    accommodating the predetermined gas and the medium, of which the porosity is desirous to be measured, in the gas vessel and the medium vessel, respectively;
    forming the second loop and maintaining it for a predetermined time;
    forming the first loop, maintaining it for a predetermined time, and measuring a concentration of the predetermined gas in the first loop by the gas component detector;
    forming the third loop, maintaining it for a predetermined time so that pores of the medium are filled with the predetermined gas, and measuring a concentration of the predetermined gas in the third loop by the gas component detector; and
    calculating porosity of the medium based on the respective gas concentrations in the first and third loops, respective internal volumes of these loops, a volume of the medium, and a mass balance equation for the predetermined gas in these loops.

13. The method according to claim 12, before the second loop is formed, the method further comprising additionally forming the first loop to measure a background concentration of the predetermined gas in the additional first loop by the gas component detector, wherein after forming the second loop, the gas concentrations measured in the first and third loops by the gas component detector are corrected by subtracting the background concentration therefrom.

14. The method according to claim 12, wherein the predetermined gas comprises at least one of radon and helium.

15. The method according to claim 12, wherein a solid substance generating the predetermined gas is accommodated in the gas vessel.

16. The method according to claim 12, wherein a drying tube is further installed on the first loop of the apparatus of measuring porosity, and before forming the second loop, the method further comprises additionally forming the first loop to allow air to circulate in the first loop, thereby removing moisture within the third loop.

17. The method according to claim 12, wherein a drying tube is further installed on the third loop of the apparatus of measuring porosity, and before forming the second loop, the method further comprises additionally forming the third loop to allow air to circulate in the third loop, thereby removing moisture within the third loop.

* * * * *